United States Patent
Gülcher et al.

(10) Patent No.: US 9,878,076 B2
(45) Date of Patent: Jan. 30, 2018

(54) ASPIRATION CATHETER

(75) Inventors: Manfred Gülcher, Raesfeld-Erie (DE); Martina Maria Schmitt, Garstedt (DE)

(73) Assignee: Qualimed Innovative Medizinprodukte GmbH, Winsen (DE)

( * ) Notice: Subject to any disclaimer, the term of this patent is extended or adjusted under 35 U.S.C. 154(b) by 0 days.

(21) Appl. No.: 14/240,674

(22) PCT Filed: Aug. 31, 2012

(86) PCT No.: PCT/EP2012/003656
§ 371 (c)(1),
(2), (4) Date: Apr. 17, 2014

(87) PCT Pub. No.: WO2013/029795
PCT Pub. Date: Mar. 7, 2013

(65) Prior Publication Data
US 2014/0214048 A1    Jul. 31, 2014

(30) Foreign Application Priority Data
Aug. 31, 2011    (DE) .......................... 10 2011 111 534

(51) Int. Cl.
*A61M 1/00*    (2006.01)
*A61M 25/01*    (2006.01)
(Continued)

(52) U.S. Cl.
CPC ........... *A61M 1/0031* (2013.01); *A61B 17/22* (2013.01); *A61M 25/003* (2013.01);
(Continued)

(58) Field of Classification Search
CPC .. A61M 2025/1056; A61M 2025/0177; A61M 2025/0183; A61M 2025/0031;
(Continued)

(56) References Cited

U.S. PATENT DOCUMENTS 5,456,680 A    10/1995    Taylor et al.
6,669,679 B1 *  12/2003    Savage ............... A61M 25/007
                                              604/131
(Continued)

FOREIGN PATENT DOCUMENTS

EP    1681075 A1    7/2006
WO    WO2010/036541 A1    4/2010

OTHER PUBLICATIONS

"90/10 & 80/20 Platinum/Iridium." H. Cross Company, 2008. Web. <https%3A%2F%2Fweb.archive.org%2Fweb%2F20081222040527%2Fhttp%3A%2F%2Fwww.hcrosscompany.com%2Fprecious%2Fplatirid.htm>.*
(Continued)

*Primary Examiner* — Imani Hayman
*Assistant Examiner* — James D Ponton
(74) *Attorney, Agent, or Firm* — Berliner & Associates (57) ABSTRACT

The invention relates to an aspiration catheter for the extraction of thrombotic maternal from blood vessels. The catheter has a first and a second lumen, the first lumen being distally provided with an aspiration opening and the second lumen having a smaller cross section than the first lumen and extending coaxially in the distal region of the first lumen. The second lumen is provided with a lateral as well as a distally located opening, the lateral opening reaching through the wall of the catheter. Within the first lumen a stabilization wire is movably arranged which terminates distally of the lateral opening of the second lumen but proximally of the aspiration opening of the first lumen.

13 Claims, 6 Drawing Sheets

(51) Int. Cl.
 *A61B 17/22* (2006.01)
 *A61M 25/00* (2006.01)
(52) U.S. Cl.
 CPC ........ *A61M 25/005* (2013.01); *A61M 25/007* (2013.01); *A61M 25/0043* (2013.01); *A61M 25/0102* (2013.01); *A61B 2017/22079* (2013.01); *A61M 25/0021* (2013.01); *A61M 25/0032* (2013.01); *A61M 25/0054* (2013.01); *A61M 25/0108* (2013.01); *A61M 2025/0031* (2013.01); *A61M 2025/0063* (2013.01); *A61M 2025/0183* (2013.01)
(58) Field of Classification Search
 CPC ........ A61M 2025/0059; A61M 25/003; A61M 25/005; A61M 25/0052; A61M 25/0067; A61M 25/0068; A61M 25/007; A61M 25/0071; A61M 1/0031; A61B 17/22; A61B 2017/22079
 See application file for complete search history.

(56) References Cited

U.S. PATENT DOCUMENTS

| | | | |
|---|---|---|---|
| 2002/0035347 A1* | 3/2002 | Bagaoisan | A61M 25/1011 604/35 |
| 2002/0177800 A1* | 11/2002 | Bagaoisan et al. | 604/6.12 |
| 2005/0240165 A1* | 10/2005 | Miki et al. | 604/528 |
| 2007/0191812 A1* | 8/2007 | Nishide et al. | 604/523 |
| 2009/0018502 A1 | 1/2009 | Reifart et al. | |
| 2010/0036312 A1* | 2/2010 | Krolik et al. | 604/22 |
| 2010/0049147 A1* | 2/2010 | Tanikawa | A61B 17/22 604/265 |

OTHER PUBLICATIONS

PCT Search Report issued Oct. 23, 2012 in connection with related PCT Application No. PCT/EP2012/003656.

\* cited by examiner

ASPIRATION CATHETER

Aspiration catheter for the extraction of thrombotic material from blood vessels with a first and a second lumen, wherein the first lumen is distally provided with an aspiration opening and the second lumen of smaller cross section than the first lumen and extending axially parallel in the distal region of the first lumen being provided with a lateral as well as distally located opening, said lateral opening reaching through the wall of the catheter.

In human blood vessels, especially in the coronary region, the formation of deposits, plaques or clots for example is frequently encountered that may obstruct or totally interrupt the flow of blood. In the event such an obstruction has formed in a supplying vessel in the coronary region very serious sequelae may occur, for instance infarction, consequential health impairments or even fatalities. As regards medical care or treatment of such patients a fast elimination of such bottlenecks or obstructions is essential.

For treatment of sclerotic deposits in vascular systems techniques are frequently adopted that embrace a dilatation of the vessel (angioplasty), for instance through the use of balloon catheters. More often than not, such techniques involve the placement of stents. In the coronary region bottlenecks or blockages are often eliminated by means of bypasses.

In case blood clots have formed or deposits of emboli are encountered aspiration catheters are commonly employed by means of which the thrombotic or embolic material is aspirated from the respective blood vessel. In the distal area said aspiration catheters are provided with an opening through which the blood is allowed to enter the catheter space. At the proximal end a customary plunger syringe is connected. With the help of said syringe a vacuum is produced so that blood with thrombotic material is extracted and passes through the catheter.

Aspiration catheters are placed in a customary manner with the aid of a guidewire. For this purpose two individual techniques have been developed which in principle have proven their worth.

The over-the-wire technique requires the aspiration catheter to be pushed onto an already placed guidewire and moved to the application site along this guidewire.

For the rapid exchange technique the aspiration catheter is provided with an additional catheter tube in the distal zone, said tube can then be pushed onto an already placed guidewire so that the aspiration catheter can be moved to the application site along the guidewire.

With the over-the-wire technique a problem exists in that the guidewire inside the aspiration catheter may impede the forward movement of the catheter towards the application site due to frictional forces arising. Moreover, the guidewire causes the aspiration lumen to be narrowed over the entire length of the catheter and in this way limits the aspiration efficiency.

As regards the rapid exchange technique the additional lumen outside the aspiration catheter is space consuming and makes maneuvering more difficult.

With a further enhancement of the rapid exchange catheter an additional lumen for the guidewire has been provided in the distal area of the aspiration catheter. Said lumen has a distal opening as well as a lateral opening so that the distal end of the aspiration catheter can be pushed onto the guidewire which then exits through the lateral opening and extends in parallel to the aspiration catheter. By this variant an aspiration catheter can be placed quickly and dead on target. On the other hand, this variant involves the risk of the aspiration catheter to become bent or folded over at its weakest point which is the lateral exit opening of the second lumen. If this takes place, the aspiration capacity of the aspiration catheter may become impaired only in the most favorable case but normally the aspiration catheter has to be replaced.

Aspiration catheters can only be fully functioning and effective if their distally located catheter tip can be successfully maneuvered through a point of constriction—usually a blood clot—and the aspiration effect being brought about only subsequently when the aspiration catheter is withdrawn. The design of the catheter tip is of the same importance in this context as the arrangement of the aspiration opening which should be provided with a lateral configuration component. These requirements must be met and correspond and harmonized with the arrangement of the lumen for the guidewire.

It is thus the objective of the present invention to provide an aspiration catheter that avoids the disadvantages of known aspiration catheters as described hereinbefore, among which in particular the bending or folding tendency of aspiration catheters working according to the rapid exchange system.

This objective is reached by the provision of an aspiration catheter of the kind first mentioned above, wherein within the first lumen a stabilization wire is movably arranged which extends distally beyond the lateral opening of the second lumen but terminates at a point ahead of the aspiration opening of the first lumen.

The inventive aspiration catheter constitutes a combination of two known principles, i.e. the over-the-wire principle and the rapid exchange principle. A first wider lumen serves the purpose of aspirating thrombotic material from the affected relevant blood vessel, with a more narrow second lumen being arranged within the first lumen extending axially parallel in the distal region of the first lumen and having a guiding function along the guidewire.

The second lumen being arranged axially parallel in the distal area of the first lumen is provided with a distal and lateral opening in such a manner that the aspiration catheter can be guided along a guidewire run through the second lumen and moved to its application site in that it virtually "rides" on the guidewire. The lateral opening extends through the catheter wall of the first lumen, the distal opening of the second lumen terminates distally of the aspiration opening of the first lumen and thus forms in particular also the distal tip of the aspiration catheter as a whole. The lateral opening is situated proximally of the aspiration opening of the first lumen, with the distance to the aspiration opening and catheter tip being arranged for such that a precise guidance of the aspiration catheter on the guide wire can be achieved. It is expedient to attach the wall of the second lumen to the inner wall of the catheter (the first lumen).

As provided for by the invention a stabilization wire is arranged within the first lumen, said wire being movably supported, respectively arranged. Basically, this stabilization wire is designed similarly to a customary guidewire which in this case is not intended for catheter guidance but rather serves to lend as much stability to the catheter moving along the guidewire as is necessary to prevent the catheter tube from being bent or folded at locations of vessel convolutions and branching off vessels. This stabilization wire extends beyond the lateral opening of the second lumen and in any case terminates proximally of the aspiration opening.

Preferably, the stabilization wire ends immediately after the lateral opening of the second lumen. It is ensured in this way that the stabilization wire does not cause additional flexibility and maneuverability impairment to the distal area of the aspiration catheter. However, since said wire reaches beyond the lateral opening of the second lumen this is sufficient to avoid buckling/bending risks in this sensitive region.

In particular, the inventive catheter is divided into four individual zones, i.e. ranging from zone A (distal) to zone D (proximal). Zone A, extending from the catheter tip to the lateral opening constitutes the aspiration region which needs a certain amount of stability so as not to collapse under conditions of reduced pressure. Zone B that adjoins zone A proximally has increased flexibility offering advantages in winding or curving vessels.

Zone C located proximally to zone B and separated from zone B by means of a transfer point where the materials of zones B and C are brought together offers good maneuverability to enable the catheter to be guided through a patient's vascular system. Zone D, the proximal sector, stands for the favorable transmission of forces, i.e. reliably passing the forces applied to the proximal end of the catheter on to the catheter tip.

The individual sections or zones are each made of materials that possess the required properties and are known basically. Materials which are frequently employed are polyamides, for instance grillamide, polyether block amide (PEBA) and blends thereof, in particular for the zones B to D as well as for the tubing of the inner lumen.

The length of the individual sections may vary within certain limits depending on the relevant requirements to be met. It is to be borne in mind in this context that increasing the length of zone B at the expense of the lengths of zones C and/or D will enhance flexibility but will result in impairing the transmission of forces and maneuverability. In a catheter provided in accordance with the invention zone A usually has a length ranging between 20 and 50 mm, zone B a length ranging between 200 and 500 mm, and zones C and D together a length of up to 1250 mm.

With respect to the inventive aspiration catheter it is preferred that the tube of the second lumen projects beyond the distal end of the first lumen and with its distal opening forms the distal end of the aspiration catheter. As the outer diameter of the tube of the second lumen is significantly smaller than that of the aspiration catheter itself this results in the distal end of the catheter projecting and taking on a nose-like shape. Shaping the catheter tip in this manner permits a clot or embolus in a blood vessel to be penetrated by this "nose-shaped" element so that the aspiration opening is then situated distally of the vessel blockage and upon withdrawal of the catheter enables the aspiration to take effect.

In general, the diameter of the second lumen is considerably smaller than that of the first lumen. Especially, the cross sectional relation between the first and the second lumen is in the range of 3:1 to 10:1, preferably in the range of 4:1 to 6:1.

As used in this application the terms "distal" and "proximal" are to be understood such that the catheter end reaching into the vessel, i.e. the end of the catheter facing away from the attending physician is the distal end while the end or side facing the physician is denoted as proximal. Point of reference is thus the attending physician or the location where the catheter enters the body of a patient, usually the groin.

The aspiration opening of the first lumen in particular also constitutes the end of the first lumen. However, preferred is an inclined or slightly laterally offset arrangement at the distal end of the catheter tube so that an aspiration effect can be produced both distally and laterally. In particular, the aspiration opening has a drop-like or oval shape.

To rule out suction through the aspiration opening taking place at a vessel wall it is expedient to arrange in the first lumen at the location and approximately on the opposite side of the aspiration opening a pressure balancing opening which is of considerably smaller size so that although it is capable of producing a pressure compensating effect if clogging of the aspiration opening has occurred it cannot reduce the suction capacity of the aspiration opening to a notable extent.

Expediently, this pressure balancing opening is laterally offset relative to the run of the second lumen.

In the interest of achieving a precise placement of aspiration catheter and, in particular, aspiration opening of the first lumen the tube of the second lumen is provided with a marker arranged at the point where the aspiration opening is located. This marker can be provided in the form of a band, sleeve, or ring and, preferably, consists of a platinum-iridium alloy 90/10 which has good radiopaque properties.

To ensure the aspiration catheter can be easily and accurately maneuvered it is considered expedient to vary the stiffness, respectively flexibility of the stabilization wire. As a rule, the proximal part of the stabilization wire is less flexible and stiffer than the distal part. Stiffness in this case may decrease continuously from proximal to distal but may also decrease in leaps.

The inventive aspiration catheter may be provided with a customary hydrophilic coating which, however, is not applied as a rule to the entire catheter but ends proximally of the lateral opening of the second lumen.

Advantageously, the stabilization wire is provided with a marker in the distal area. For the attending physician this marker serves the purpose of indicating that when the stabilization wire is retracted to clear the aspiration route the end of the stabilization wire is located outside said aspiration route. Normally, the aspiration syringe is connected to the catheter via a Y-connector and a luerlock so that the end of the stabilization wire should be located beyond the Y-branch. An appropriate distance to the distal end of the stabilization wire and, where appropriate, a pre-marking are considered useful.

It may also be useful to increase the thickness of the distal end of the stabilization wire slightly so that it can only be pulled out fully when exerting increased force; additionally, the proximal area of the catheter may be slightly narrowed so that the thickened portion of the stabilization wire can be suitably intercepted.

The marking also furnishes information about the length of the stabilization wire remaining in the catheter, said length must not interfere with or impair the aspiration process.

To conclude with, the invention relates to an aspiration catheter of the kind described herein as a set also comprising an appropriately sized guidewire and guiding catheter as well as a syringe, where applicable or required, for the purpose of aspirating blood that contains thrombotic material.

As per a preferred embodiment the distal area of the first lumen has an oval or ellipsoidal cross section, wherein the aspiration opening is located at the side of the main axis of the oval or ellipse. The distal area of the inventive aspiration catheter is pressed flat, with an aspiration opening being arranged at the flat side opposite to the second lumen. This configuration has the effect that the aspiration opening cannot readily adapt or adjust to the vessel wall which reduces the risk of the opening clinging or adhering to the wall. Moreover, the aspiration opening made wider in this manner permits thrombotic material to be aspirated more thoroughly, in particular when in the form of plaque.

Elucidation of the invention is provided by the following figures where.

Figure 1:
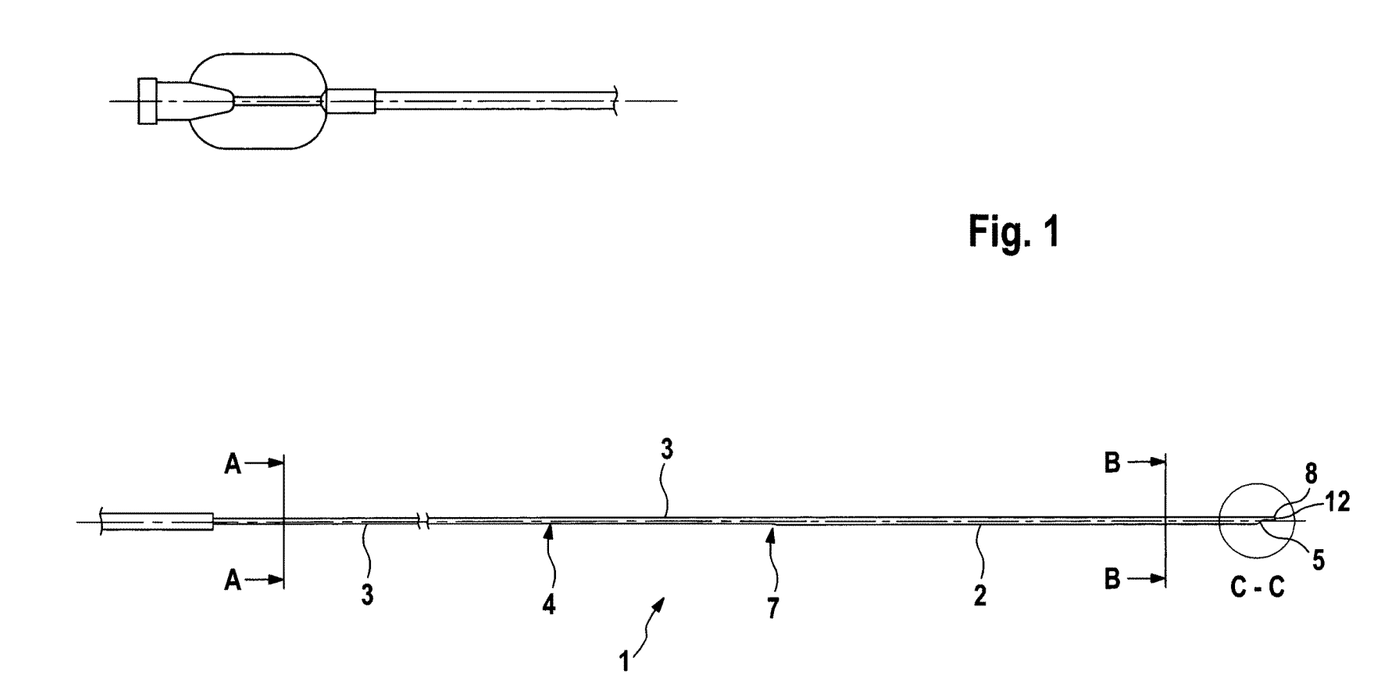
FIG. 1 is an overall representation of the inventive aspiration catheter.

FIG. 1 shows an aspiration catheter 1 provided by the invention, comprising the first lumen 3, the distal area 2 of the first lumen as well as the aspiration opening 5. Proximally, the aspiration catheter is provided with customary devices for the insertion through a conventional Y-connector.

The catheter is of customary size, for example has an outer diameter of 1.37 mm and an inner diameter of 1.10 mm. It is made of customary materials, for instance Peba, polyamide or combinations thereof, wherein the catheter itself may consist of different materials for different sections so as to suit requirements with respect to stiffness and flexibility. For example, the catheter depicted in FIG. 1 is made of a stiffer material in the proximal area up to the transition point 4, whereas it is of a less stiff material distally from the transition point 4. This makes it easier to insert/introduce it into a vascular system. Zone B commences distally of transition point 4, extends up to the inlet opening 7 of the second lumen 6, and possesses higher flexibility.

Figure 2A:
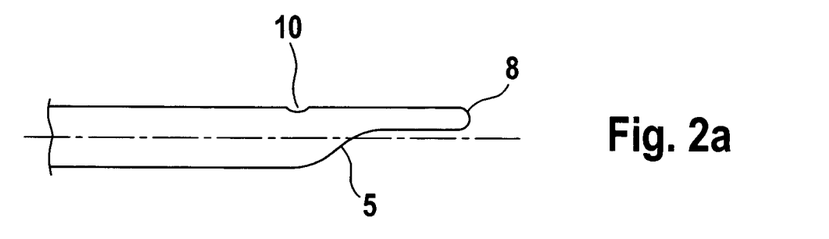
FIG. 2*a* shows the tip area C-C of the catheter shown in FIG. 1 from the side and FIG. 2*b* from below.
Figure 2B:
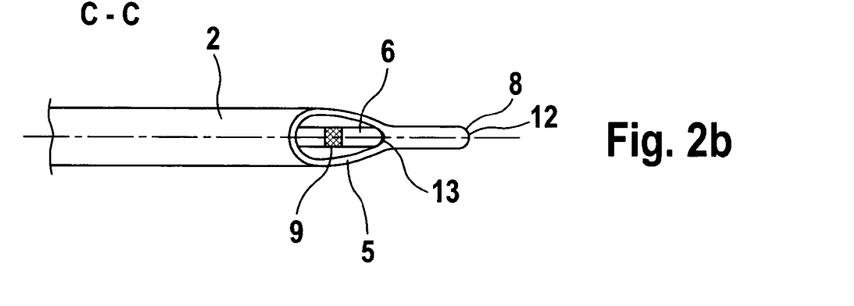

The catheter in accordance with the invention has a distal area 2 starting at the inlet opening 7 of the second lumen 6 and extending up to the catheter tip. The distal area coincides with zone A and, for example, has a length of 30 mm. The second lumen 6 extends inside said distal area 2 (see FIG. 2), with said second lumen terminating in distal opening 8 which is coincident with the catheter tip 12. Below catheter tip 12 and second lumen 6 the aspiration opening 5 is arranged, which has been slightly offset proximally.

Detail C-C is shown in FIGS. 2*a* and 2*b* and illustrates the catheter tip from the side (a) as well as from below (b). As can be seen from the side view the terminating second lumen with its opening 8 takes on a nose-like shape forming the catheter tip 12. Aspiration opening 5 is located below said nose-like shape, with a pressure balancing hole 10 being arranged oppositely which does not serve aspiration purposes but is only intended as pressure compensating element in particular to prevent the aspiration opening from attaching itself to a vessel wall.

FIG. 2*b* illustrates the detail C-C of FIG. 1 from below, that is from the side of the aspiration opening 5. The detail shows the distal end 12 of the catheter which also forms the distal end and the distal opening 8 of the second lumen 6. A tube extending along the opposite side of the distal area 2 constitutes the second lumen 6. The second lumen 6 is provided with a marker sleeve 9 made of Pt—Ir 90/10 which serves as orientation aid for the attending physician.

The second lumen 6 is arranged along the side of distal area 2 of the catheter 1 opposite the aspiration opening 5. It can be seen that the diameter of the second lumen 6 is considerably smaller than that of the first lumen 3 or the distal area 2. The nose formed by the distal end 12 of the lumen 6 extends beyond the distal end 13 of the first lumen and serves to initially penetrate an existing blood clot with the help of the aspiration catheter and then aspirate and extract thrombotic material upon retraction of the aspiration catheter.

Figure 3A:
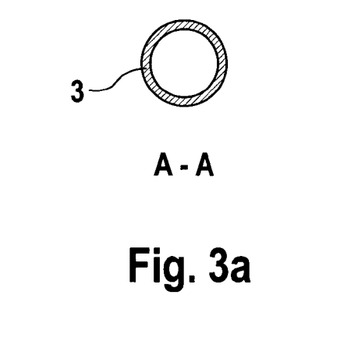
FIG. 3*a* is a cross section of the catheter of FIG. 1 at location A-A.

FIG. 3*a* illustrates the cross section of the aspiration catheter 1 at location A-A. The catheter has an outer diameter of 1.37 mm in this case and an inner diameter of 1.10 mm and consists of a flexible tube made of plastic material approved for medical purposes, for instance Pebax, polyamide or Teflon or mixtures thereof.

Figure 3B:
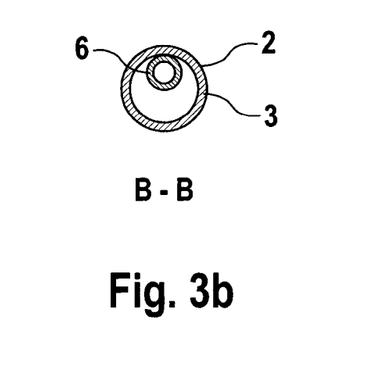
FIG. 3*b* shows the distal area of the catheter at location B-B in FIG. 1 as cross sectional view.

FIG. 3*b* depicts section B-B of the distal area 2 of the aspiration catheter proposed in accordance with the invention. Said figure shows the first lumen 3 of the aspiration catheter as well as the second lumen 6 which serves for catheter guidance via a rapid exchange guidewire. The second lumen has an inner diameter of 0.42 mm and an outer diameter of 0.57 mm so that it is significantly smaller than the first lumen. Advantageously, the tube of the second lumen 6 is secured to the inner wall of the tube of the first lumen 3. Accordingly, the cross sectional ratio thus amounts to about 5:1 (first to second lumen).

Figure 4:
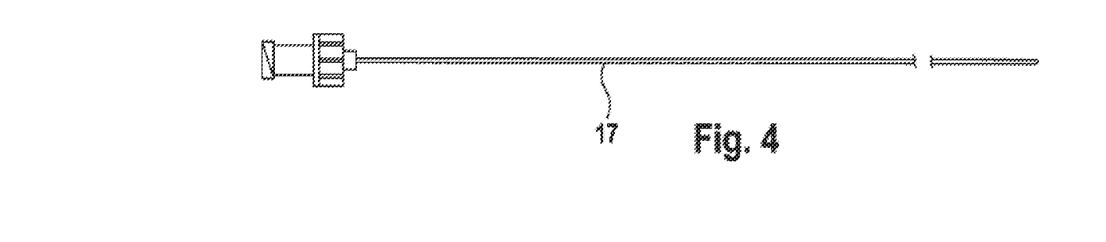
FIG. 4 illustrates the stabilization wire.

FIG. 4 shows the stabilization wire with insertion aid, said wire for example has a length of 1400 mm, a diameter of 0.62 mm and is made of customary spring steel, i.e. of approximately the same material as is used for a customary guidewire.

Figure 5:
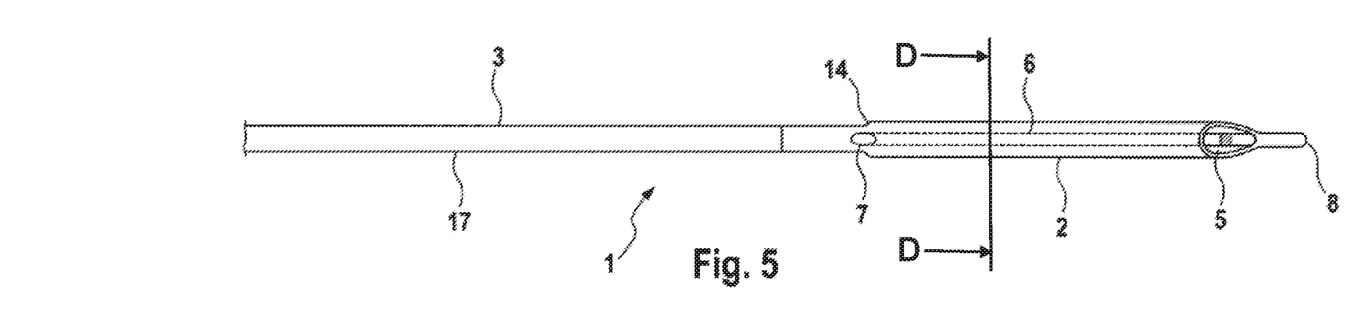
FIG. 5 is a detail representation of the end region of the catheter of FIG. 1.

From FIG. 5 the distal area 2 of the inventive aspiration catheter 3 can be seen. The figure illustrates the lateral opening 7 which represents the proximal end of the internally arranged second lumen 6 shown as a broken line, said lumen forming the catheter tip 12 and terminating at the distal opening 8. Moreover, aspiration opening 5 can be seen behind which marker sleeve 9 of the lumen 2 is visible. Proximal to lateral opening 7 the catheter is provided with a hydrophilic coating 17.

Figure 5A:
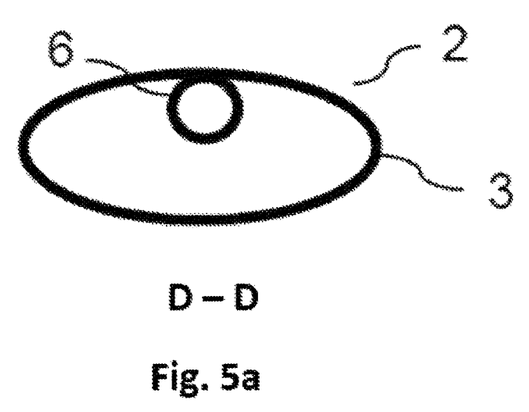
FIG. 5*a* shows the distal area of the catheter at location D-D in FIG. 5 as a cross sectional view.

In distal area 2 the first lumen 3 of the inventive aspiration catheter preferably has a shape which can be referred to as "pressed flat" in such a manner that the cross section is roughly oval or ellipsoidal. This shape starts approximately at the point where the lateral opening 7 of the second lumen 6 is located and is represented in the figure as diminished step 14. Accordingly, in the distal area the catheter 1 has a main axis transversely to its run or extension that is longer, and a shorter auxiliary axis extending vertically to the main axis, here seen in viewing direction. In this way, the distal area 2 takes on the form of a sword. Aspiration opening 5 is arranged on a broad side of the sword.

It is to be understood that the lateral opening 7 of the second lumen 6 may also be arranged on the side opposite aspiration opening 5 of the distal area 2, respectively catheter 1.

Figure 6:
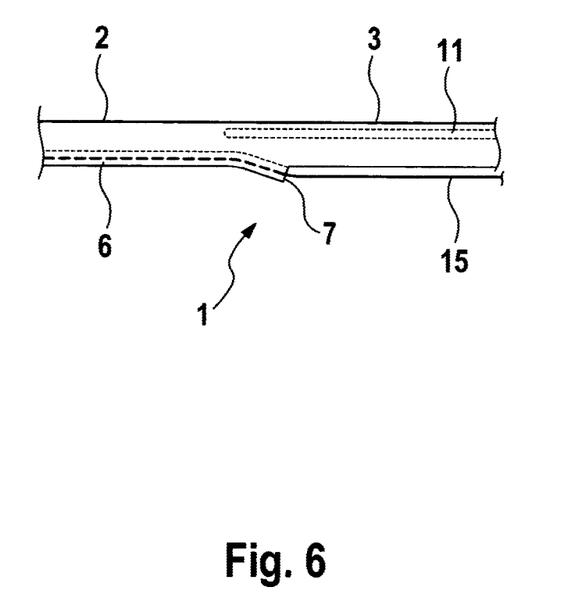
FIG. 6 elucidating the interaction of catheter, stabilization wire, guidewire, and second lumen

FIG. 6 shows a section of an inventive catheter 1 in the region of transition towards distal area 2. Inside the first lumen 3 the second lumen 6 is arranged with lateral opening 7. Inside the first lumen 3 the stabilization wire 11 extends and terminates distally of lateral opening 7. Inside lumen 6 a guidewire 15 is arranged which exits from the catheter 1 through lateral opening 7. In the area of lateral opening 7 the stabilization wire 11 and the guidewire 15 extend in parallel over a short distance, approximately 5 to 10 mm, which increases the stiffness and thus resistance to bending/buckling of the catheter 1 at this location sensitive in that regard.

Figure 7:
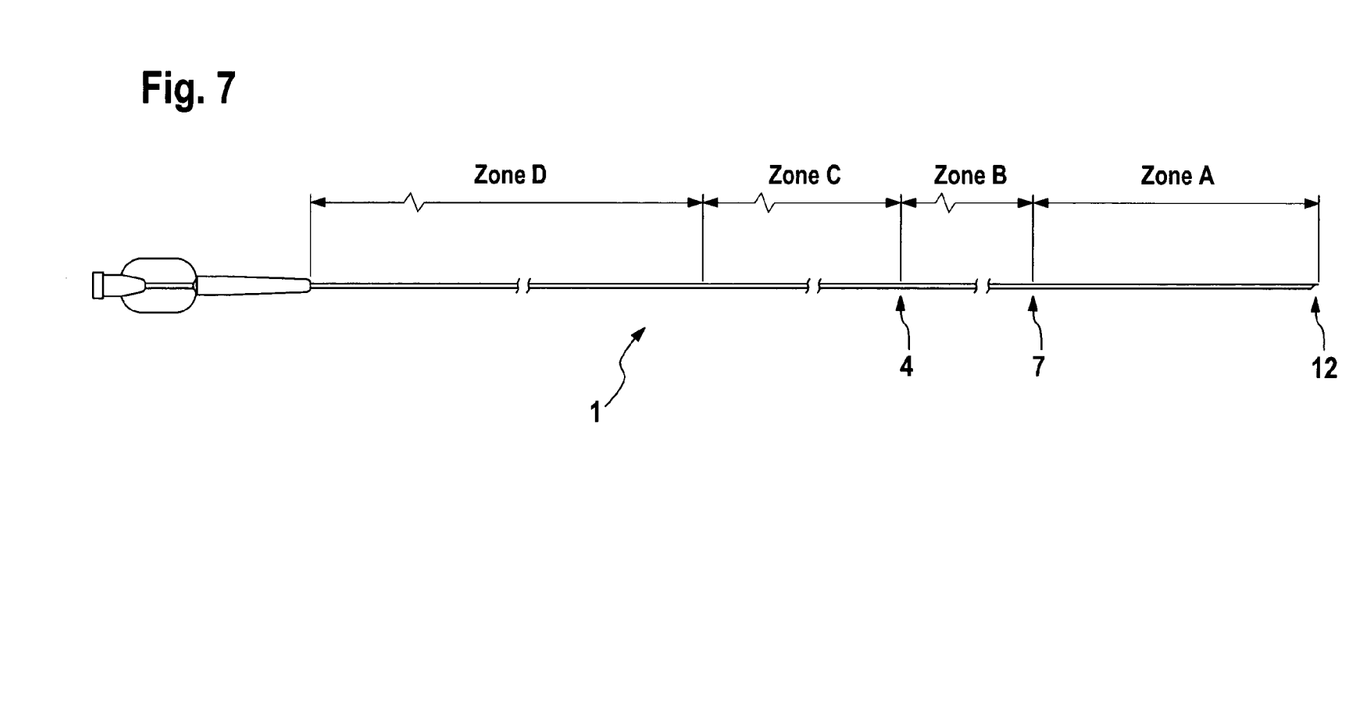
FIG. 7 shows the sectionalized design of an inventive catheter.

In FIG. 7 an inventive aspiration catheter 1 is illustrated with the transition point 4, lateral opening 7, and catheter tip 12, also showing the zone division described hereinbefore.

Zone A is the distal zone and has a length of about 30 mm. Zone A represents the aspiration section which is characterized by increased resistance to pressure.

Proximally adjoining zone A is zone B which offers increased flexibility. Zone B extends from transition point 4 up to the lateral opening 7.

The increased flexibility of zone B makes it easier to guide the system in convoluting vessels, for instance in the coronary region.

Proximally to zone B and adjoining the transition point 4 zone C is located offering good maneuverability, i.e. is suited to follow without difficulty twisting vessel configurations over longer distances. The proximally adjoining zone D consists of a material that enables forces to be well transmitted up to the tip of the catheter.

The invention claimed is:

1. An aspiration catheter for the extraction of thrombotic material from blood vessels, the catheter comprising:
    a tip,
    a first lumen defined by a wall of the catheter,
    first and second opposite ends,
    a distal region at the first end of the catheter comprising a shape with an oval or ellipsoidal cross section, wherein the first lumen is distally provided with an aspiration opening in the distal region,
    a proximal region at the second end of the catheter,
    a second lumen defined by the catheter, the second lumen having a smaller cross-sectional area than the first lumen and extending axially parallel to the first lumen in the distal region of the catheter, the second lumen being provided with a lateral opening as well as a distally located opening, said lateral opening reaching through the catheter wall that defines the first lumen,
    a stabilization wire within the first lumen movably arranged and which terminates distally of the lateral opening of the second lumen but proximally of the aspiration opening of the first lumen,
    the aspiration catheter being divided into four zones A-D wherein:
        zone A extends from the catheter tip to the lateral opening to constitute an aspiration region, a pressure balancing opening being situated in zone A opposite the aspiration opening and capable of producing a pressure compensating effect if clogging of the aspiration opening has occurred but without an operationally significant reduction of the suction capacity of the aspiration opening,
        zone B is located proximally of zone A and has increased flexibility relative to zone A,
        zone C is located proximally to zone B and is separated from zone B by means of a transfer point where the materials of zones B and C are brought together whereby to provide enhanced maneuverability to enable the catheter to be guided through a patient's vascular system,
        and zone D, which is located proximally to zone C, passes forces applied to the second end of the catheter on to the catheter tip.

2. The aspiration catheter according to claim 1, in which the stabilization wire terminates immediately distally of the lateral opening of the second lumen.

3. The aspiration catheter according to claim 1, in which the first lumen has a distal end wherein the second lumen projects beyond the distal end of the first lumen and with the distally located opening forms the tip of the aspiration catheter.

4. The aspiration catheter according to claim 1, in which the second lumen has an outer cross section, the tip of the aspiration catheter being designed so as to have a nose-like shape and outer cross section coinciding with the outer cross section of the second lumen.

5. The aspiration catheter according to claim 1 in which the first lumen has a distal end, the aspiration opening being arranged laterally or obliquely at the distal end of the first lumen.

6. The aspiration catheter according to claim 5, in which the aspiration opening is situated opposite the second lumen.

7. The aspiration catheter according to claim 1, in which the pressure balancing opening is offset laterally with respect to the second lumen.

8. The aspiration catheter according to claim 1, comprising a marker ring on the second lumen, said ring being arranged adjacent the aspiration opening of the first lumen.

9. The aspiration catheter according to claim 8 in which the marker ring is made of platinum-iridium alloy 90/10.

10. The aspiration catheter according to claim 1, in which the stabilization wire has a flexibility that increases from proximal to distal.

11. The aspiration catheter according to claim 1, comprising an outer hydrophilic coating.

12. The aspiration catheter according to claim 11, in which the hydrophilic coating ends proximally to the lateral opening of the second lumen.

13. The aspiration catheter according to claim 1, in which the stabilization wire has a proximal and distal area and a predetermined length and is provided with a marking on the distal area, whereby when the stabilization wire is extracted from the catheter, said marking indicates a length of the stabilization wire that was in the catheter.

* * * * *